United States Patent
Lee et al.

(10) Patent No.: US 12,303,307 B2
(45) Date of Patent: May 20, 2025

(54) SEMICONDUCTOR DEVICE MEASUREMENT METHOD USING X-RAY SCATTERING AND SEMICONDUCTOR DEVICE MANUFACTURING METHOD INCLUDING THE MEASUREMENT METHOD

(71) Applicant: SAMSUNG ELECTRONICS CO., LTD., Suwon-si (KR)

(72) Inventors: Jaeyong Lee, Suwon-si (KR); Hidong Kwak, Suwon-si (KR); Minjung Shin, Suwon-si (KR); Seungryeol Oh, Suwon-si (KR); Chuhee Lee, Suwon-si (KR); Byunghyun Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 291 days.

(21) Appl. No.: 18/095,926

(22) Filed: Jan. 11, 2023

(65) Prior Publication Data

US 2023/0380783 A1    Nov. 30, 2023

(30) Foreign Application Priority Data

May 30, 2022    (KR) .................. 10-2022-0066351

(51) Int. Cl.
*A61B 6/00*    (2006.01)
(52) U.S. Cl.
CPC ................ *A61B 6/44* (2013.01); *A61B 6/483* (2013.01)
(58) Field of Classification Search
CPC .................................. A61B 6/44; A61B 6/483
See application file for complete search history.

(56) References Cited

U.S. PATENT DOCUMENTS

| | | |
|---|---|---|
| 7,110,491 B2 | 9/2006 | Mazor et al. |
| 9,846,132 B2 | 12/2017 | Bakeman et al. |
| 9,885,962 B2 | 2/2018 | Veldman et al. |
| 9,915,522 B1 | 3/2018 | Jiang et al. |
| 10,352,695 B2 | 7/2019 | Dziura et al. |
| 10,983,073 B2 | 4/2021 | Ogata et al. |
| 11,181,489 B2 | 11/2021 | Thompson et al. |
| 2015/0300965 A1* | 10/2015 | Sezginer .............. G01N 23/207 378/86 |
| 2021/0207956 A1 | 7/2021 | Shchegrov et al. |

FOREIGN PATENT DOCUMENTS

KR    1020200131545 A    11/2020

* cited by examiner

*Primary Examiner* — Dani Fox
*Assistant Examiner* — Fani Polyzos Boosalis
(74) *Attorney, Agent, or Firm* — Sughrue Mion, PLLC

(57) ABSTRACT

A semiconductor device measurement method using X-ray scattering includes preparing a semiconductor device including a repeat structure, irradiating X-rays onto the semiconductor device to obtain a first X-ray scattering image, calculating a second X-ray scattering image through simulation, the second X-ray scattering image corresponding to a target repeat structure for the semiconductor device, generating a repeat structure mask by analyzing a position of a signal for a regular repeat structure from the second X-ray scattering image, removing the repeat structure mask from the first X-ray scattering image and generating an error image; and analyzing the error image and calculating irregularities for the repeat structure of the semiconductor device.

20 Claims, 15 Drawing Sheets

(4 of 15 Drawing Sheet(s) Filed in Color)

SEMICONDUCTOR DEVICE MEASUREMENT METHOD USING X-RAY SCATTERING AND SEMICONDUCTOR DEVICE MANUFACTURING METHOD INCLUDING THE MEASUREMENT METHOD

CROSS-REFERENCE TO RELATED APPLICATION

This application is based on and claims priority under 35 U.S.C. § 119 to Korean Patent Application No. 10-2022-0066351, filed on May 30, 2022, in the Korean Intellectual Property Office, the disclosure of which is incorporated by reference herein in its entirety.

BACKGROUND

The present disclosure relates to a semiconductor device measurement method, and more particularly, to a semiconductor device measurement method using X-ray scattering and a semiconductor device manufacturing method including the semiconductor device measurement method.

Semiconductor devices such as logic and memory devices may be manufactured through a series of semiconductor processes. In addition, in order to detect defects on the wafer and realize a higher yield, measurement of a semiconductor device may be made during a semiconductor process. As a semiconductor device measurement method, related art imaging techniques, such as transmission electron microscopes (TEMs), scanning electron microscopes (SEMs), and the like, are used together with destructive sample preparation techniques. For example, TEMs may achieve high resolution levels and measure to any depth, but require disruptive cutting of samples and a long process time. In addition, to describe the characteristics of critical dimensions, film thickness, composition, and other parameters of nanoscale structures, measurement methods including scatterometry, reflectometry, and associated analysis algorithms are used. For example, a scatterometry critical dimension (SCD) method is used for a target composed of periodic repeat structures.

SUMMARY

It is an aspect to provide a semiconductor device measurement method using X-ray scattering capable of accurately measuring irregularities generated in an actual process with respect to a semiconductor device including a repeat structure, and a semiconductor device manufacturing method including the semiconductor device measurement method.

According to an aspect of some embodiments, there is provided a semiconductor device measurement method comprising preparing a semiconductor device including a repeat structure, irradiating X-rays onto the semiconductor device to obtain a first X-ray scattering image, calculating a second X-ray scattering image through simulation, the second X-ray scattering image corresponding to a target repeat structure for the semiconductor device, generating a repeat structure mask by analyzing a position of a signal for a regular repeat structure from the second X-ray scattering image, removing the repeat structure mask from the first X-ray scattering image and generating an error image; and analyzing the error image and calculating irregularities for the repeat structure of the semiconductor device.

According to another aspect of one or more embodiments, there is provided a semiconductor device measurement method comprising loading a wafer into a small-angle X-ray scattering (SAXS) measurement device; measuring a semiconductor device in the wafer with the SAXS measurement device; storing a first X-ray scattering image for the semiconductor device; modeling a target repeat structure for the semiconductor device; analyzing X-rays with respect to the modeled target repeat structure; storing a second X-ray scattering image with respect to the target repeat structure; and removing the second X-ray scattering image from the first X-ray scattering image and calculating structural irregularities of a repeat structure of the semiconductor device in an X-ray measurement field of view (FoV), wherein the irregularities represent a difference between an actual repeat structure of the semiconductor device and the target repeat structure.

According to another aspect of some embodiments, there is provided a semiconductor device manufacturing method comprising preparing a semiconductor device including a repeat structure; irradiating X-rays onto the semiconductor device to obtain a first X-ray scattering image; calculating a second X-ray scattering image through simulation, the second X-ray scattering image corresponding to a target repeat structure for the semiconductor device; generating a repeat structure mask from the second X-ray scattering image by analyzing a position of a signal for a regular repeat structure; removing the repeat structure mask from the first X-ray scattering image and generating an error image; analyzing the error image and calculating irregularities for the repeat structure of the semiconductor device; and applying the irregularities to a process dispersion management of the semiconductor device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments will be more clearly understood from the following detailed description taken in conjunction with the accompanying drawings in which.

DETAILED DESCRIPTION

Figure 1:
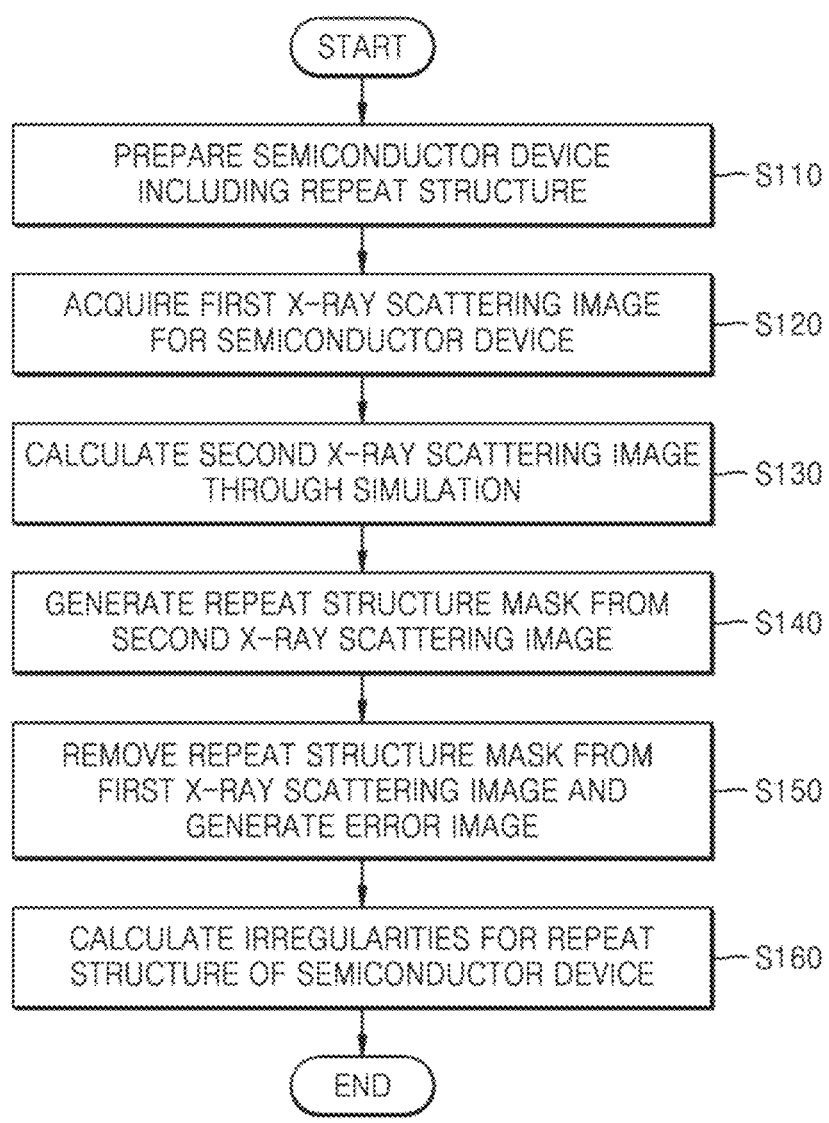
FIG. 1 is a flowchart schematically illustrating a process of a method of measuring a semiconductor device using X-ray scattering, according to some embodiments.

Hereinafter, various embodiments will be described in detail with reference to the accompanying drawings. The same reference numerals are used for the same components in the drawings, and redundant descriptions thereof will be omitted.

FIG. 1 is a flowchart schematically illustrating a process of a method of measuring a semiconductor device using X-ray scattering according to some embodiments, and FIGS. 2A to 2D are photos of X-ray scattering images for explaining the method of measuring the semiconductor device of FIG. 1.

Figure 2A:
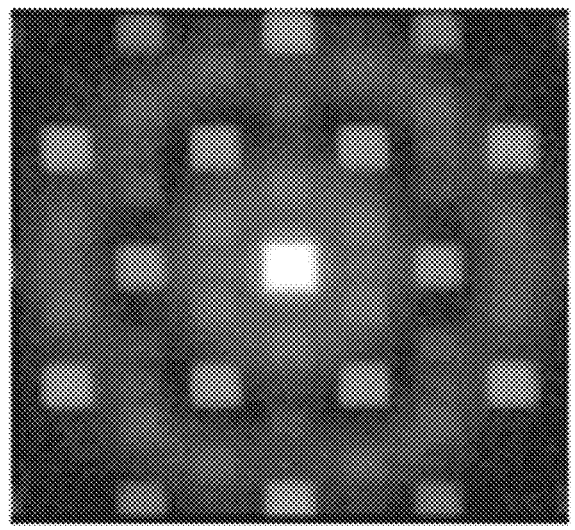
FIGS. 2A to 2D are photos of X-ray scattering images for explaining the method of measuring a semiconductor device of FIG. 1, according to some embodiments.

Referring to FIGS. 1 to 2A, a semiconductor device measurement method (hereinafter, simply referred to as a "semiconductor device measurement method") using X-ray scattering includes preparing a semiconductor device including a repeat structure (S110). The repeat structure may be a repetitive structure that is repeated at regular intervals over the semiconductor device, as illustrated in FIG. 2A. The semiconductor device may include a repeat structure of a high aspect ratio (HAR). The semiconductor device may include, for example, a spin transfer torque random access memory (STT-RAM), a vertical NAND (VNAND) memory, a dynamic random access memory (DRAM), a three-dimensional flash (3D-FLASH) memory, a resistive random access memory (Re-RAM), a phase change random access memory (PC-RAM), or the like.

In the semiconductor device measurement method according to some embodiments, the semiconductor device may be a DRAM or VNAND memory. For example, in the case of DRAM, the repeat structure may include a storage node. In the case of the VNAND memory, the repeat structure may include a channel hole. However, the type and repeat structure of the semiconductor device are not limited to the above-described devices and repeat structures.

In operation S110 of preparing a semiconductor device, the semiconductor device may be prepared in a wafer level. In other words, in the measurement of the repeat structure of the semiconductor device, a wafer having a plurality of semiconductor devices each including the corresponding repeat structure may be prepared. In some embodiments, an individual semiconductor device to be measured, not a wafer, may be prepared.

A first X-ray scattering image of the semiconductor device is acquired (S120). The first X-ray scattering image may be obtained through small-angle X-ray scattering (SAXS) measurement using a SAXS measurement device 100 (see FIG. 6A) of a SAXS facility 1000 (see FIG. 6A). The photo of FIG. 2A may correspond to the first X-ray scattering image of the semiconductor device. It may be seen that the center is the brightest due to the diffraction phenomenon, the bright parts of the reinforcement interference appear at the outer edge in response to the diffraction order, and the farther from the center, the darker the parts of the reinforcement interference become. A more detailed configuration of the SAXS facility will be described in more detail with reference to FIG. 6A.

For reference, SAXS measurement may be used to measure structural and material properties in relation to a manufacturing process of a semiconductor device. For example, SAXS measurement may be used to measure critical dimensions, thickness, overlay, material properties, etc. of a semiconductor structure having a high aspect ratio (HAR). This SAXS measurement may include irradiating an X-ray onto a measurement target, i.e., a sample, and detecting the intensity of a diffraction order that appears after the X-ray is reflected for one or more incident angles. That is, the intensity of the diffraction order may be detected for one or more incident angles. As a specific example, SAXS measurements may be performed over a certain range of incident angles that provide sufficient resolution and penetration depth to describe the characteristics of the overall depth of a HAR structure.

In SAXS measurements, when measurements are made in one or more non-vertical directions of the X-ray, particularly in directions near vertical incidence, a phenomenon in which the X-ray diffraction signal is strong and affected in a unique way may be utilized. When a high-brightness X-ray source is used, high-flux X-ray penetration may be possible into an opaque region of a target of the sample. Geometric shape parameters measurable through SAXS measurements may include, for example, pore size, pore density, line edge illumination, line width illumination, sidewall angle, profile, critical dimensions, overlay, edge placement error, pitch, and the like. In addition, material parameters that may be measured through SAXS measurement may include, for example, electron density. Furthermore, SAXS measurements may be used to measure advanced semiconductor devices such as STT-RAM, V-NAND, DRAM, PC-RAM, and Re-RAM, which require measurement of geometric shape parameters and material parameters as well as features less than 10 nm.

In SAXS measurements, the vertically manufactured structure of HAR may diffract the irradiated X-rays with multiple diffraction orders. Each diffraction order moves in a particular predictable direction, and the angle interval of the diffraction order may be inversely proportional to the lattice constant of the sample divided by the wavelength. This diffraction order may be individually detected by a detector array arranged at a certain distance from the wafer. Each pixel of the detector outputs a signal indicating the number of photons colliding with the pixel, and outputs of pixels belonging to the same diffraction order may be combined with each other.

The intensity of the diffraction order may be expressed as $I(m, n, q, j, \lambda)$. Here, $\{m, n\}$ is an integer index of the diffraction order. $\{q, j\}$ is the azimuth and elevation angle of the incident X-ray (i.e., the polar coordinates of the incident main ray with respect to the coordinate system fixed to the wafer). $\lambda$ is the wavelength of the incident X-ray. The intensity of the diffracted X-ray may be collected as a function of the X-ray incident angle with respect to the normal line of the wafer surface. Information included in a plurality of diffraction orders may be unique in each model parameter. Accordingly, X-ray scattering may be used to calculate an estimation result for a value of a required parameter.

Figure 2B:
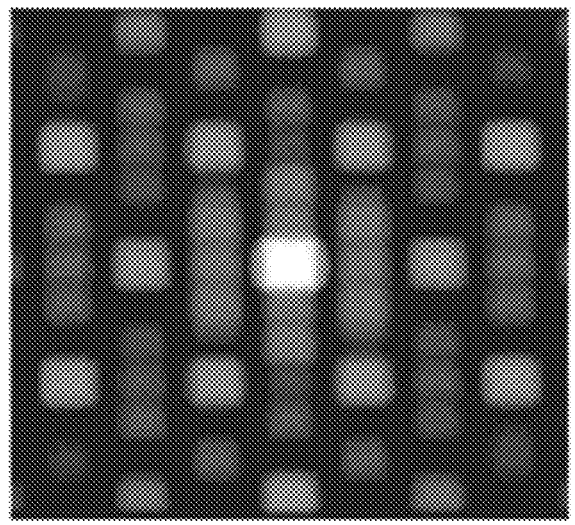

Referring to FIGS. 1 to 2B, a second X-ray scattering image is then calculated through simulation (S130). Here, the simulation may be a simulation for calculating an X-ray scattering image corresponding to a repeat structure. Accordingly, an X-ray scattering image corresponding to a repeat structure included in the semiconductor device, that is, a target repeat structure, may be calculated through simulation. The photo of FIG. 2B may correspond to the second X-ray scattering image calculated by the simulation.

For reference, the first X-ray scattering image is a scattering image obtained by measuring a repeat structure included in an actual semiconductor device with a SAXS measurement device, and the second X-ray scattering image is a scattering image of a target repeat structure that is required to be formed in a semiconductor device. Therefore, if the repeat structure is accurately formed in the actual semiconductor device, the first X-ray scattering image and the second X-ray scattering image may be substantially the same. However, due to various causes during the semiconductor process, a target repeat structure may not be formed in an actual semiconductor device, and thus the first X-ray scattering image and the second X-ray scattering image are different from each other.

Figure 2C:

Referring to FIGS. 1 to 2C, a repeat structure mask is generated from the second X-ray scattering image (S140). For example, the repeat structure mask may be generated by analyzing a position of a signal with respect to the repeat structure from the second X-ray scattering image. In other words, in the second X-ray scattering image, a repeat structure mask including bright parts corresponding to a position where the intensity of the X-ray is measured by diffraction, that is, a part of reinforcing interference is generated. In some embodiments, in the second X-ray scattering image, a repeat structure mask consisting of bright parts corresponding to the position where the intensity of the X-ray is measured by diffraction is generated. In some embodiments, The photo of FIG. 2C may correspond to an image of the repeat structure mask.

For reference, the second X-ray scattering image of FIG. 2B, similar to the first X-ray scattering image of FIG. 2A, is the brightest at the center due to diffraction, and parts of reinforcing interference become darker toward the outside. On the contrary, in the case of the repeat structure mask, all portions corresponding to the reinforcement interference may include similar brightness. The reason for separately generating a repeating structure mask in which the part of reinforcement interference is brightly displayed is to obtain an error image more clearly in the operation of calculating the error image later. That is, in the operation of calculating the error image, when the second X-ray scattering image is used as it is, the error image may not be clear in a dark part of the outer edge of the reinforcement interference parts.

Figure 2D:
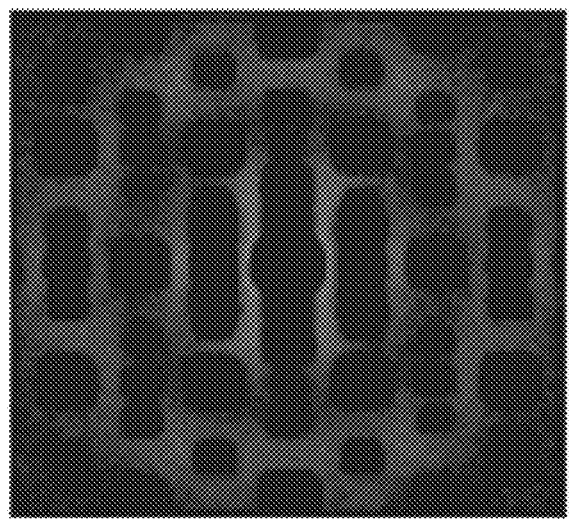

Referring to FIGS. 1 to 2D, the repeat structure mask is removed from the first X-ray scattering image and an error image is generated (S150). That is, an error image is generated by subtracting a bright portion of the reinforcement interference of the repeat structure mask from the first X-ray scattering image. The photo of FIG. 2D may correspond to an error image. In the photo of FIG. 2D, black parts may be parts of reinforcing interference of the repeat structure mask, and slightly bright parts between the black parts may be parts corresponding to a difference signal between the first X-ray scattering image and the repeat structure mask. If there is no error in the first X-ray scattering image, the entire error image may appear dark.

Thereafter, irregularities with respect to the repeat structure of the semiconductor device are calculated (S160). For example, irregularities with respect to the repeat structure of the semiconductor device may be calculated by analyzing the error image. In the semiconductor device measurement method, irregularities with respect to the repeat structure of the semiconductor device may be numerically quantified based on the error image. Quantification of irregularities with respect to the repeat structure of the semiconductor device will be described in more detail with reference to FIGS. 3A to 4.

The semiconductor device measurement method according to some embodiments includes the processes of the generation of the second X-ray scattering image through simulation, the generation of the repeat structure mask, the generation of the error image, and the calculation of the irregularities based on the error image. For semiconductor devices including a repeat structure, it is possible to accurately measure the irregularities in the actual process.

In general, structural measurement using X-rays may measure a representative value of a repeat structure in a field of view (FoV). Therefore, structural measurement using X-rays may be used to target the center value of the module target specification (MTS), but the dispersion of the repeat structure within the FoV may not be obtained. Although scanning electron microscope (SEM) may be used to measure the dispersion of the repeat structure, SEM has a limitation in that SEM can only reach a few hundred nm from the surface even when high acceleration is used.

In contrast, the semiconductor device measurement method according to some embodiments may be used to accurately calculate the dispersion value for the repeat structure of the entire upper and lower parts in the FOV using the X-ray. Accordingly, the semiconductor device measurement method of some embodiments may be used to measure the repeat structure of HAR in a semiconductor process. For example, the semiconductor device measurement method of some embodiments may be used to measure a repeat structure in a storage node process of DRAM and/or a channel hole process of VNAND.

Figure 3A:
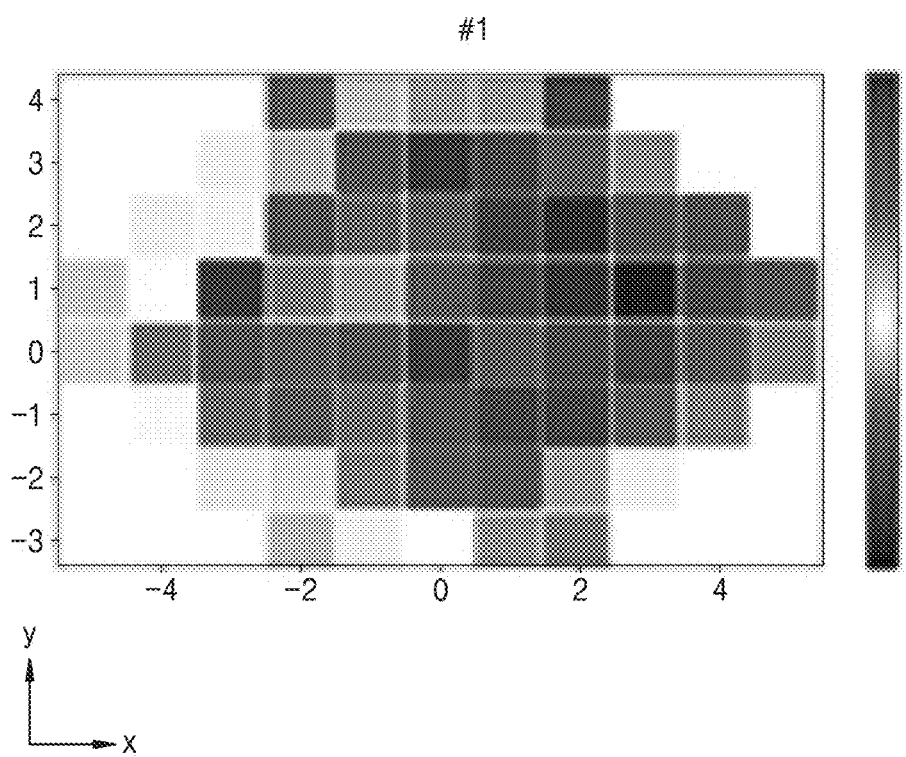
FIGS. 3A to 3D are simulation photos obtained by quantifying irregularities obtained by the method of measuring a semiconductor device of FIG. 1, according to some embodiments.
Figure 3B:
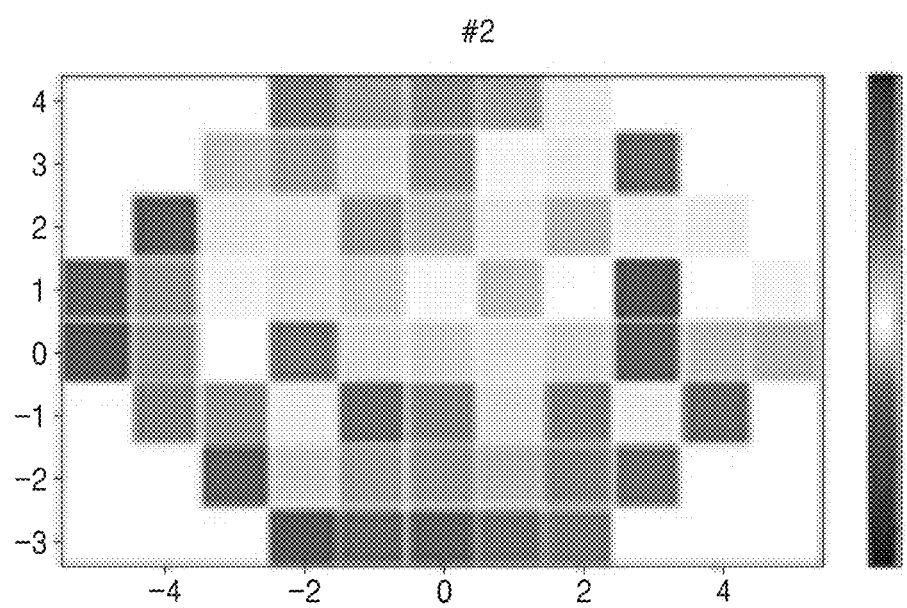
Figure 3C:
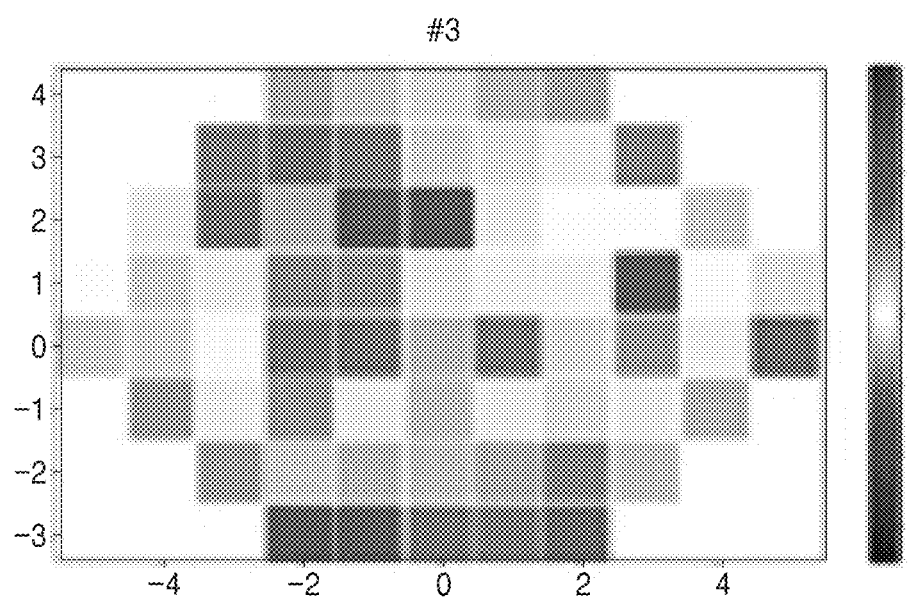
Figure 3D:
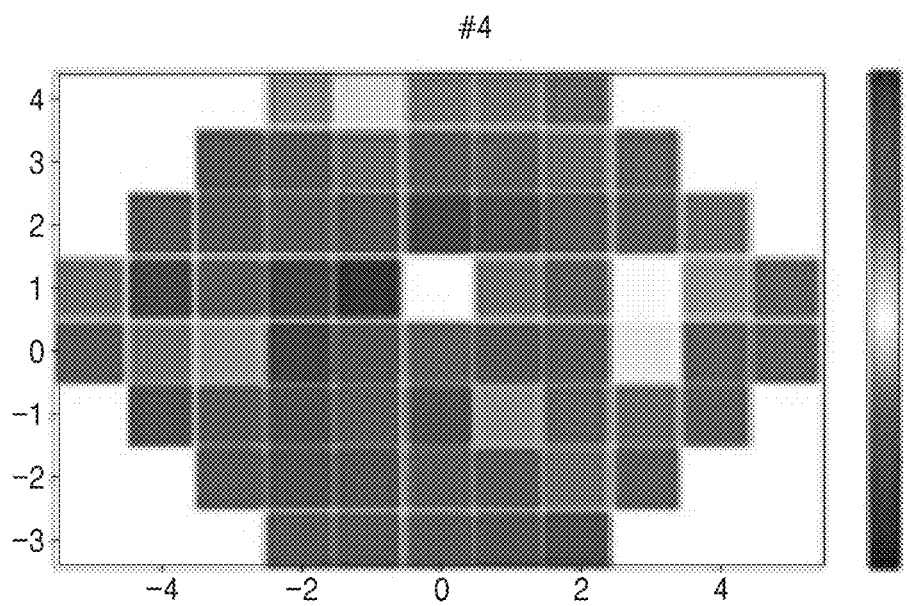
Figure 4:
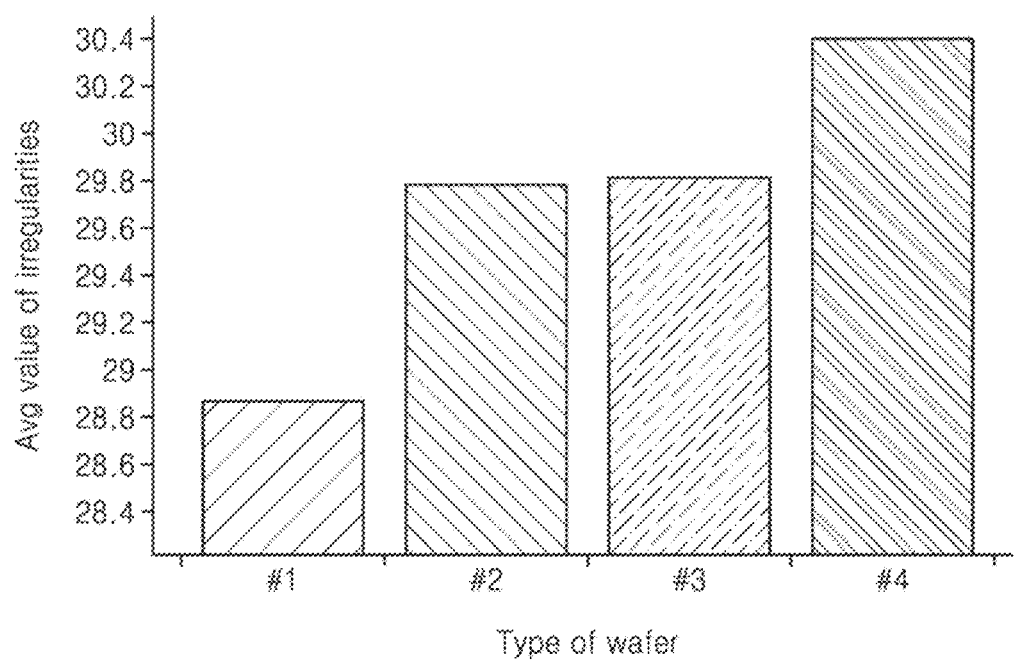
FIG. 4 is a graph showing irregularities corresponding to the simulation photos of FIGS. 3A to 3D as average values, according to some embodiments.

FIGS. 3A to 3D are simulation photos obtained by quantifying irregularities obtained by the method of measuring the semiconductor device of FIG. 1, according to some embodiments, and FIG. 4 is a graph showing irregularities corresponding to the simulation photos of FIGS. 3A to 3D as average values. In FIGS. 3A to 3D, the x-axis and the y-axis represent positions on the wafer, and the light and shade of the black-and-white represents a relative value for irregularities. In FIG. 4, the x-axis represents the type of wafers in FIGS. 3A to 3D, and the y-axis represents the average value of irregularities.

Referring to FIGS. 3A to 3D, FIGS. 3A to 3D may correspond to simulation photographs in which irregularities with respect to a repeat structure are numerically quantified based on an error image. In each of FIGS. 3A to 3D, the bar graph on the right side is a black-and-white processing of colors, in which the lower side corresponds to the blue series, the upper side corresponds to the red series, and the middle part corresponds to the white series. In addition, the blue series may correspond to a value with small irregularities, and the red series may correspond to a value with large irregularities. In other words, the irregularities may be greater from bottom to top in the bar graph.

Although black-and-white treatment is performed and looks similar, in FIG. 3A, dark black corresponds to a blue series, and in FIG. 3D, dark black corresponds to a red series. Accordingly, it may be seen that irregularities of the semiconductor devices of the wafer of FIG. 3A are relatively small and irregularities of the semiconductor devices of the wafer of FIG. 3D are relatively large. In the case of the wafers of FIGS. 3B and 3C, although there is a slight difference in each of the positions, it may be seen that the wafers have similar irregularities as a whole.

Quantification of irregularities may be accomplished in a variety of ways. For example, in the semiconductor device measurement method of some embodiments, irregularities of the repeat structure may be calculated as an average value with respect to a distance based on the center of the error image or calculated and quantified as a value obtained by applying a weight to a distance from the center. Specifically, in the error image of FIG. 2D, irregularities may be quantified numerically by allocating values corresponding to distances from the center with respect to each of regions corresponding to the difference signal, and averaging the values. If there are few regions corresponding to the difference signal, the value for irregularities becomes small. In addition, even when regions corresponding to the difference signal exist only in the center portion, the value for irregularities becomes small. On the contrary, if there are many regions corresponding to the difference signal far from the center, the value for irregularities increases. In the case of the weight application method, the brightness of the regions corresponding to the difference signal is too low to contribute to the calculation of irregularities, as a position becomes farther from the center, and thus the contribution of the regions corresponding to the difference signal of the outer part may be reinforced by adding weight.

Referring to FIG. 4, the average value of irregularities of the wafer #1 corresponding to FIG. 3A is the lowest, and the average value of irregularities of the wafer #4 corresponding to FIG. 3D is the highest. In addition, it may be seen that the average values of irregularities of the wafers #2 and #3 corresponding to FIGS. 3B and 3C are moderate and similar to each other. The average value of the irregularities of FIG. 4 may be obtained by averaging values for the irregularities allocated to the semiconductor devices (square) of each of the wafers #1 to #4 of FIGS. 3A to 3D. For example, in the bar graphs on the right sides of FIGS. 3A to 3D, the lower blue series may be about 28.5, the upper red series may be about 30.5, and the middle white system may be about 29.5. Accordingly, in the case of the wafer #1 of FIG. 3A, since most of the semiconductor devices are blue-based, the average value of irregularities is about 28.8, and in the case of the wafer #4 of FIG. 3D, since most of the semiconductor devices are red-based, the average value of irregularities is about 30.4.

The simulation photos and the graph of the average value of the irregularities of FIGS. 3A to 4 may correspond to results obtained from the dielectric film process of the storage nodes of the DRAM. For example, in the dielectric film process of the storage node of the DRAM, the amount of bending randomly generated in the storage node of the DRAM increases as the dielectric film post-processing process time increases, and such results may be confirmed through the simulation photos and the graph of the average value of irregularities of FIGS. 3A to 4. Accordingly, it is possible to confirm the expected tendency between design of experimental (DoE) wafers using the semiconductor device measurement method of some embodiments. As a result, the semiconductor device measurement method according to some embodiments may contribute to improving process dispersion of the HAR structure like a storage node of DRAM and thus reducing product development time.

Figure 5:
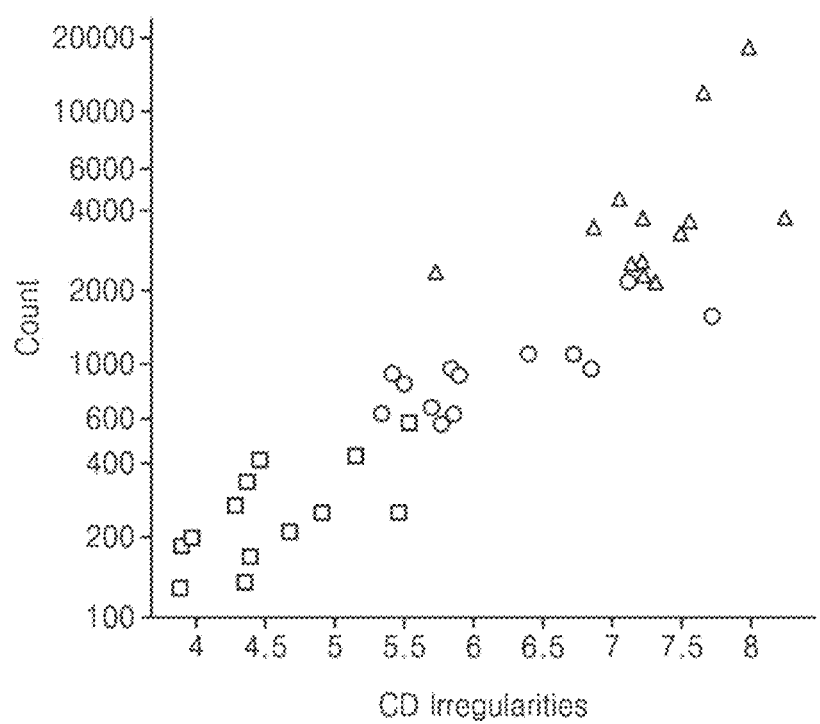
FIG. 5 is a graph illustrating a correlation between a defective semiconductor device and irregularities of a CD, according to some embodiments.

FIG. 5 is a graph illustrating a correlation between a defective semiconductor device and irregularities of a critical dimension (CD). The x-axis represents the irregularities of the CD, the y-axis represents the number of defective dies, and the square, triangle, and circle may mean different process conditions.

Referring to FIG. 5, as may be seen from the graph of FIG. 5, it may be seen that the number of defective dies increases as the irregularities of the CD increases. For reference, in the graph of FIG. 5, the irregularities of the CD are digitized by the dispersion value of the CD, and the defective dies may refer to dies in which an electrical die sort (EDS) storage node bridge disturb (SBD) defect occurs. As a result, it may be seen from the graph of FIG. 5 that there is a close correlation between the irregularities of the CD and the defective dies.

It may be seen that, in the square process condition, the irregularities of the CD is small and the number of defective dies is small, and in the triangular process condition, the irregularities of the CD is large and the number of defective dies is large. Accordingly, it may be seen that irregularities of the CD and the number of defective dies may be reduced by adjusting the process conditions. As a result, the irregularities of the repeat structure, such as irregularities of the CD, is accurately measured through the semiconductor device measurement method of some embodiments, and based on this, the process condition is appropriately adjusted, thereby minimizing the defect rate of the semiconductor device and increasing the yield of the production.

Figure 6A:
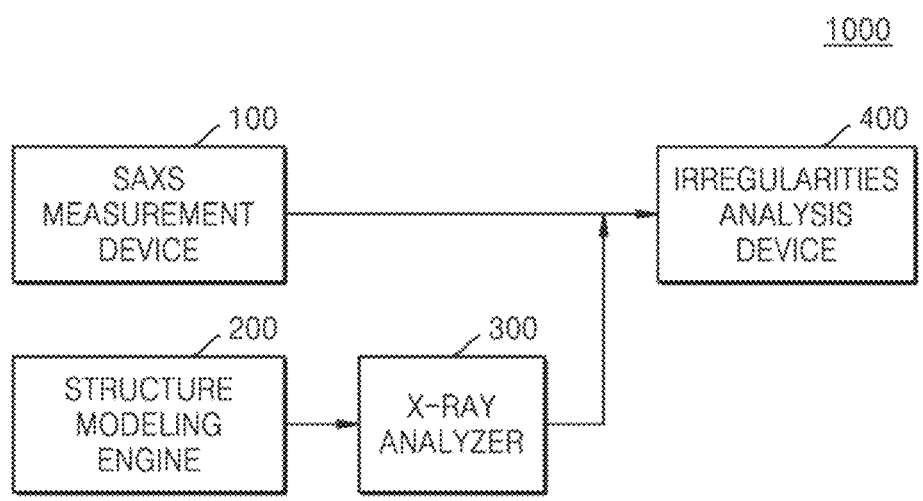
FIG. 6A is a structural block diagram schematically illustrating components of a small-angle X-ray scattering (SAXS) facility used in the method of measuring a semiconductor device of FIG. 1, according to some embodiments.
Figure 6B:
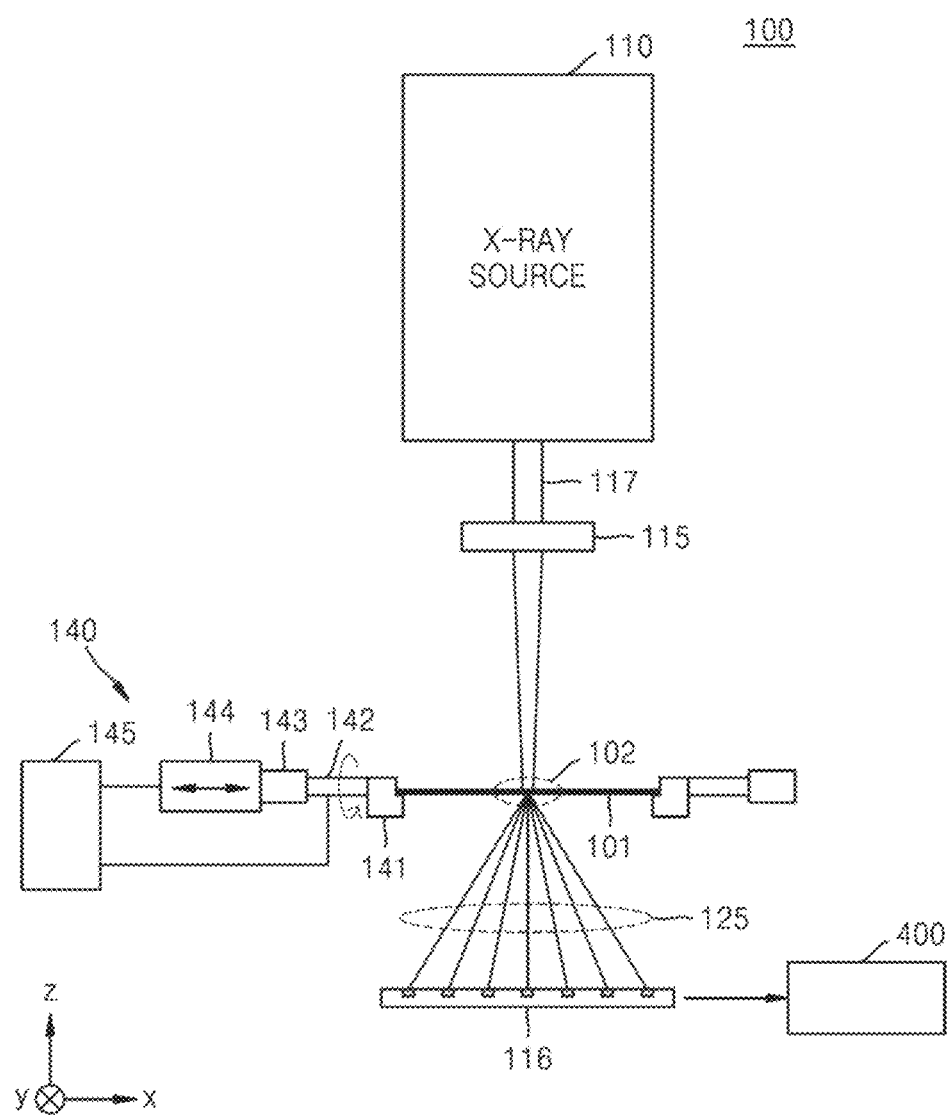
FIG. 6B is a conceptual diagram illustrating an SAXS measurement device in the SAXS facility of FIG. 6A in more detail, according to some embodiments.

FIG. 6A is a structural block diagram schematically illustrating components of a small-angle X-ray scattering (SAXS) facility used in the method of measuring the semiconductor device of FIG. 1, according to some embodiments, and FIG. 6B is a conceptual diagram illustrating an SAXS measurement device in more detail in the SAXS facility of FIG. 6A. Portions already described in the description of FIGS. 1 to 5 will be briefly described or omitted for conciseness.

Referring to FIG. 6A, the semiconductor device measurement method of some embodiments may measure a semiconductor device of a measurement target by using the SAXS facility 1000. The SAXS facility 1000 may include an SAXS measurement device 100, a structure modeling engine 200, an X-ray analyzer 300, and an irregularities analysis device 400. The SAXS measurement device 100 may be a computer processing device for generating an X-ray scattering image. The computer processing device may be, for example, a microprocessor, microcontroller, or hardware logic configured to generating the X-ray scattering image. The SAXS measurement device 100 may generate an X-ray scattering image by performing SAXS measurement on a measurement object, that is, a sample (see 101 in FIG. 6B). The SAXS measurement device 100 will be described in more detail in the following description of FIG. 6B.

The structure modeling engine 200 may be a computer processing device for performing simulation. The computer processing device may be, for example, a microprocessor, microcontroller, or hardware logic configured to perform simulation. The structure modeling engine 200 may model a repeat structure through simulation. In other words, the structure modeling engine 200 may model various types of repeat structures to be formed in the semiconductor device. For example, in the semiconductor device measurement method of some embodiments, the structure modeling engine 200 may model a repeat structure for a storage node of DRAM and/or a repeat structure for a channel hole of VNAND.

The X-ray analyzer 300 may be a computer processing device for analyzing an X-ray scattering phenomenon. The computer processing device may be, for example, a microprocessor, microcontroller, or hardware logic configured to analyze the X-ray scattering phenomenon. The X-ray analyzer 300 may analyze an X-ray scattering phenomenon with respect to the repeat structure modeled by the structure modeling engine 200. For the X-ray analyzer 300, for example, rigorous coupled-wave analysis (RCWA) or the like may be used. The analysis simulation used in the X-ray analyzer 300 is not limited to RCWA. In the semiconductor device measurement method according to some embodiments, the X-ray analyzer 300 may analyze an X-ray scattering phenomenon with respect to a repeat structure to generate an X-ray scattering image corresponding to the corresponding repeat structure. In some embodiments, the X-ray analyzer 300 may include an image generation tool for generating a repeat structure mask from the X-ray scattering image. Here, the repeat structure mask may be substantially the same as the repeat structure mask described in the repeat structure mask generation operation S140 of FIG. 1.

The irregularities analysis device 400 may be a computer processing device for analyzing irregularities. The computer processing device may be, for example, a microprocessor, microcontroller, or hardware logic configured to analyze the irregularities. The irregularities analysis device 400 may calculate irregularities by comparing and analyzing the X-ray scattering image from the SAXS measurement device 100 with the X-ray scattering image from the X-ray analyzer 300. For example, as described in the semiconductor device measurement method of FIG. 1, the irregularities analysis device 400 may generate an error image using the first X-ray scattering image and the repeat structure mask, and analyze the error image to calculate irregularities with respect to the repeat structure of the semiconductor device. In some embodiments, the irregularities analysis device 400 may quantify irregularities with respect to the repeat structure of the semiconductor device, as described in the description of FIGS. 3A to 4. The SAXS measurement device 100, the structure modeling engine 200, the X-ray analyzer 300, and the irregularities analysis device 400 are each described above as being a computer processing device. However, in some embodiments, the SAXS measurement device 100, the structure modeling engine 200, the X-ray analyzer 300, and the irregularities analysis device 400 may be implemented on a single computer processing device. That is, a computer processing device may be programmed to implement the functionality of the SAXS measurement device 100, the structure modeling engine 200, the X-ray analyzer 300, and the irregularities analysis device 400.

Referring to FIG. 6B, the SAXS measurement device 100 may include an X-ray source 110 and a sample positioning device 140. In some embodiments, although not shown, SAXS measurement device 100 may further include a computing device, as described above.

The SAXS measurement device 100 of some embodiments may include a high flux level high-brightness X-ray source 110 capable of in-line measurement of high throughput in order to provide X-ray illumination for SAXS measurement. In the SAXS measurement device 100 according to some embodiments, the X-ray source 110 may include a tunable monochromator capable of adjusting wavelengths. In SAXS measurement device 100 of some embodiments, the X-ray source 110 may include an electron beam source configured to stimulate X-rays by impacting a solid or liquid target.

For example, the X-ray source 110 may include any one of a particle accelerator source, a liquid anode source, a rotating anode source, a stationary solid anode source, a microfocus source, a microfocus rotating anode source, and a reverse Compton source. However, the X-ray source 110 is not limited to the sources described above.

For SAXS measurement, the X-ray from the X-ray source 110 may be collimated downward with a divergence of less than 1 miliradian using multi-layer X-ray optics. In the SAXS measurement device 100 according to some embodiments, SAXS measurement may be performed without using a screen positioned between the X-ray source 110 and the measurement target, that is, the sample 101. For such examples, a distribution map (i.e., an image) of the material properties (e.g., composite refractive index, electron density, or absorption rate) of a sample 101 may be obtained through measured intensity, multiple wavelengths, or a combination of both of the measured intensity and the multiple wavelengths of diffraction orders over a certain range of incident angles.

In some embodiments, to improve the collimation of the X-ray, a pinhole or aperture may be located on an opaque screen located between the X-ray source 110 and the sample 101. In such examples, the strength of the diffraction pattern may be measured for various positions of the aperture. In some other examples, a screen with a pseudo random aperture pattern is used, and the diffraction pattern may be measured for multiple screens. In the case of methods of arranging such an aperture, it may be considered to provide additional information to determine the three-dimensional distribution of the material properties of sample 101.

In the SAXS measurement device 100 of some embodiments, an X-ray optical device 115 may be included to collimate or focus X-ray on an inspection region 102 of the sample 101 with divergence of less than 1 miliradian. The X-ray optical device 115 may include diffraction optics, such as one or more x-ray collimating mirrors, X-ray aperture, X-ray beam stop, refracted X-ray optics, and zone plates, specular X-ray optics, such as a grazing incidence ellipsoidal mirror, polycapillary optics, such as hollow capillary X-ray waveguides, and multilayer optics or systems, or any combination thereof.

The X-ray detector 116 may detect the X-ray 125 scattered from the sample 101. In some embodiments, the X-ray detector 116 may generate an output signal indicating the properties of the sample 101 sensitive to the incident X-ray 117 according to the SAXS measurement aspect along with collection of the X-ray 125 scattered from the sample 101. In some embodiments, the X-ray detector 116 may decompose one or more X-ray photon energies and generate signals for each X-ray energy component representing the properties of the sample 101.

In some embodiments, the X-ray detector 116 may include any one of a CCD array, a microchannel plate, a photodiode array, a microstrip proportional counter, a gas filled proportional counter, a scintillator, and a fluorescent material. In some embodiments, the X-ray detector may include a single photon counting detector that detects the locations and number of detected photons. In some configurations, the X-ray detector 116 may be maintained in the same atmospheric environment (e.g., a gas purge environment) as the sample 101. In some embodiments, the X-ray detector 116 may be maintained in a localized vacuum environment separated from sample 101 by a vacuum window.

In the SAXS measurement device 100 of some embodiments, the sample positioning device 140 may determine the position of the sample 101 and orient the sample 101 to generate an angle-decomposed scattered X-ray. The sample positioning device 140 may include an edge grip chuck 141, a rotary actuator 142, a peripheral frame 143, a linear actuator 144, and a motion controller 145. The edge grip chuck 141 may be coupled to the sample 101 to fix the sample 101, and the rotation actuator 142 may rotate the peripheral frame 143 to rotate the edge grip chuck 141 coupled to the peripheral frame 143 and the fixed sample

101. The linear actuator 144 may translate the sample 101 in the linear direction by translating the peripheral frame 143 in the linear direction.

Specifically, the rotary actuator 142 may rotate the sample 101 around the x-axis. The rotary actuator 142 may also rotate the sample 101 around the y-axis. In addition, the rotary actuator 142 may rotate the sample 101 relative to the Z-axis, and the rotation of the sample 101 relative to the z-axis may correspond to rotation in the plane of the sample 101.

The motion controller 145 may control the rotary actuator 142 and the linear actuator 144. Through the rotary actuator 142 and the linear actuator 144, all positions on the surface of the sample 101 may be used for SAXS measurement with a predetermined incident angle.

In the SAXS measurement device 100 of some embodiments, for example, the sample positioning device 140 may include a goniometer stage, a hexapod stage, an angular stage, and a linear stage. However, the sample positioning device 140 is not limited to those described above.

The SAXS measurement device 100 of some embodiments may include a computing device that performs processing to determine an attribute of a sample based on a signal acquired by the X-ray detector 116. For example, the computing device may include a processor and a memory. The computing device may be communicatively coupled to the X-ray detector 116. According to some embodiments, the computing device may be included in the irregularities analysis device 400. In some embodiments, the irregularities analysis device 400 may be included as part of the computing device of the SAXS measurement device 100.

As described above, in SAXS measurement, the vertically manufactured structure of the HAR may diffract the collimated X-rays with multiple diffraction orders. Each diffraction order moves in a particular predictable direction, and the angle interval of the diffraction order may be inversely proportional to the lattice constant of the sample divided by the wavelength. The diffraction order is detected separately by a detector array arranged at a certain distance from a wafer, each pixel of the detector may output a signal indicative of the number of photons colliding on the pixel, and the outputs of the pixels belonging to the same diffraction order may be combined with one another.

The intensity of the diffraction order may be expressed as $I(m, n, q, j, \lambda)$. Here, $\{m, n\}$ is an integer index of the diffraction order. $\{q, j\}$ is the azimuth and elevation angle of an incident beam (i.e., the polar coordinates of the incident main ray with respect to the coordinate system fixed to the wafer). $\lambda$ is the wavelength of the incident X-ray. The intensity of the diffracted radiation may be collected as a function of the X-ray incident angle with respect to the normal line of the wafer surface. Information included in a plurality of diffraction orders may be unique in each model parameter. Thus, X-ray scattering allows calculation of estimation results for the values of the noted parameters correlated with small errors and reduced parameters.

In some embodiments, the SAXS measurement device 100 may use the computing device to generate a structural model (e.g., a geometric shape model, a material model, or a combined geometry and material model) of the measured structure of the sample. In some embodiments, the SAXS measurement device 100 may generate a SAXS response model including at least one geometric shape parameter from the structural model. In some embodiments, the SAXS measurement device 100 may perform fitting analysis of the SAXS measurement data using the SAXS response model, and may determine at least one sample parameter value through fitting analysis. In some embodiments, SAXS measurement device 100 may be used to determine material properties such as the electron density of the sample as well as geometric shape properties of the sample.

Figure 7:
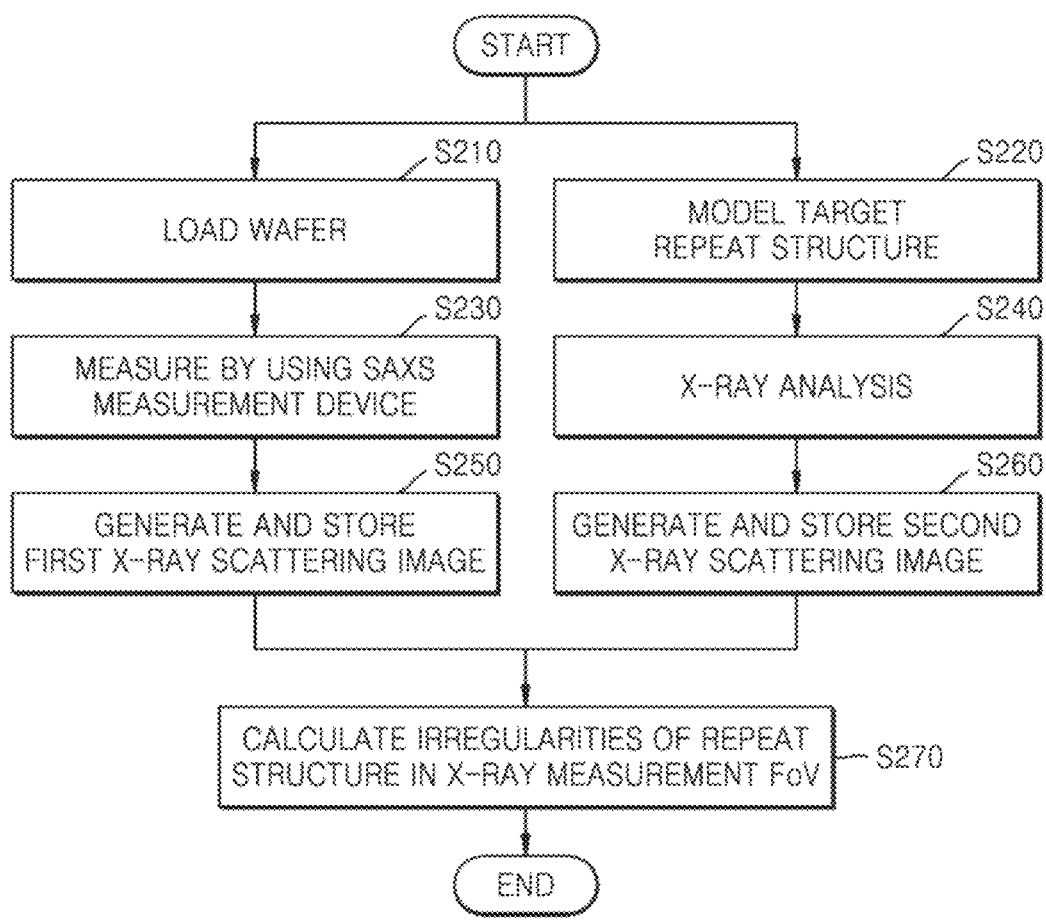
FIG. 7 is a flowchart schematically illustrating a process of a method of measuring a semiconductor device using X-ray scattering, according to some embodiments.

FIG. 7 is a flowchart schematically illustrating a process of a method of measuring a semiconductor device according to some embodiments. FIGS. 6A and 6B will be described together, and the descriptions already described in the description of FIGS. 1 to 6B will be briefly described or omitted for conciseness.

Referring to FIG. 7, the semiconductor device measurement method of some embodiments first loads the wafer to the SAXS measurement device 100 (S210). The wafer may include a plurality of semiconductor devices which are targets to be measured. According to an embodiment, individual semiconductor devices may be loaded on the SAXS measurement device 100.

Thereafter, the semiconductor device is measured by the SAXS measurement device 100 (S230), and a first X-ray scattering image for the semiconductor device is generated and stored (S250). The generation of the first X-ray scattering image for the semiconductor device is the same as described in the first X-ray scattering image acquisition operation S120 of the semiconductor device measurement method of FIG. 1.

The target repeat structure is modeled (S220). Here, the target repeat structure may be a repeat structure to be implemented in a semiconductor device. Such modeling may be performed using the structure modeling engine 200 of the SAXS facility 1000. Thereafter, X-ray analysis is performed through the X-ray analyzer 300 (S240), and a second X-ray scattering image is generated and stored based on the X-ray analysis (S260). The generation of the second X-ray scattering image is the same as described in the second X-ray scattering image acquisition operation S130 of the semiconductor device measurement method of FIG. 1. In some embodiments, the operation S260 of generating and storing the second X-ray scattering image may include an operation of generating a repeat structure mask.

In some embodiments, the loading of the wafer S210, the measuring with the SAXS measurement device S230, and the generating and storing of the first X-ray scattering image S250 may be executed in parallel with the modeling of the target repeat structure S220, the analyzing of the X-ray S240, and the generating and storing of the second X-ray scattering image S260. In some embodiments, the loading of the wafer S210, the measuring with the SAXS measurement device S230, and the generating and storing of the first X-ray scattering image S250 may be executed first, and then the modeling of the target repeat structure S220, the analyzing of the X-ray S240, and the generating and storing of the second X-ray scattering image S260 may be executed. In some embodiments, the modeling of the target repeat structure S220, the analyzing of the X-ray S240, and the generating and storing of the second X-ray scattering image S260 may be first executed, and then the loading of the wafer S210, the measuring with the SAXS measurement device S230, and the generating and storing of the first X-ray scattering image S250 may be also executed. In some embodiments, the loading of the wafer S210, the measuring with the SAXS measurement device S230, and the generating and storing of the first X-ray scattering image S250 may be executed simultaneously with execution of the modeling of the target repeat structure S220, the analyzing of the X-ray S240, and the generating and storing of the second X-ray scattering image S260.

After generating and storing the first X-ray scattering image and the second X-ray scattering image, irregularities of the repeat structure in the X-ray measurement FoV is calculated (S270). The calculation of irregularities of the repeat structure in the X-ray measurement FoV may be substantially the same as described in operation S160 of calculating irregularities of the repeat structure of the semiconductor device of the semiconductor device measurement method of FIG. 1. In other words, only the term "semiconductor device" is changed to "X-ray measurement FoV". In some embodiments, the calculation of irregularities of the repeat structure in the X-ray measurement FoV may include digitizing and quantifying the irregularities, as described in the description of FIGS. 3A to 4.

Figure 8:
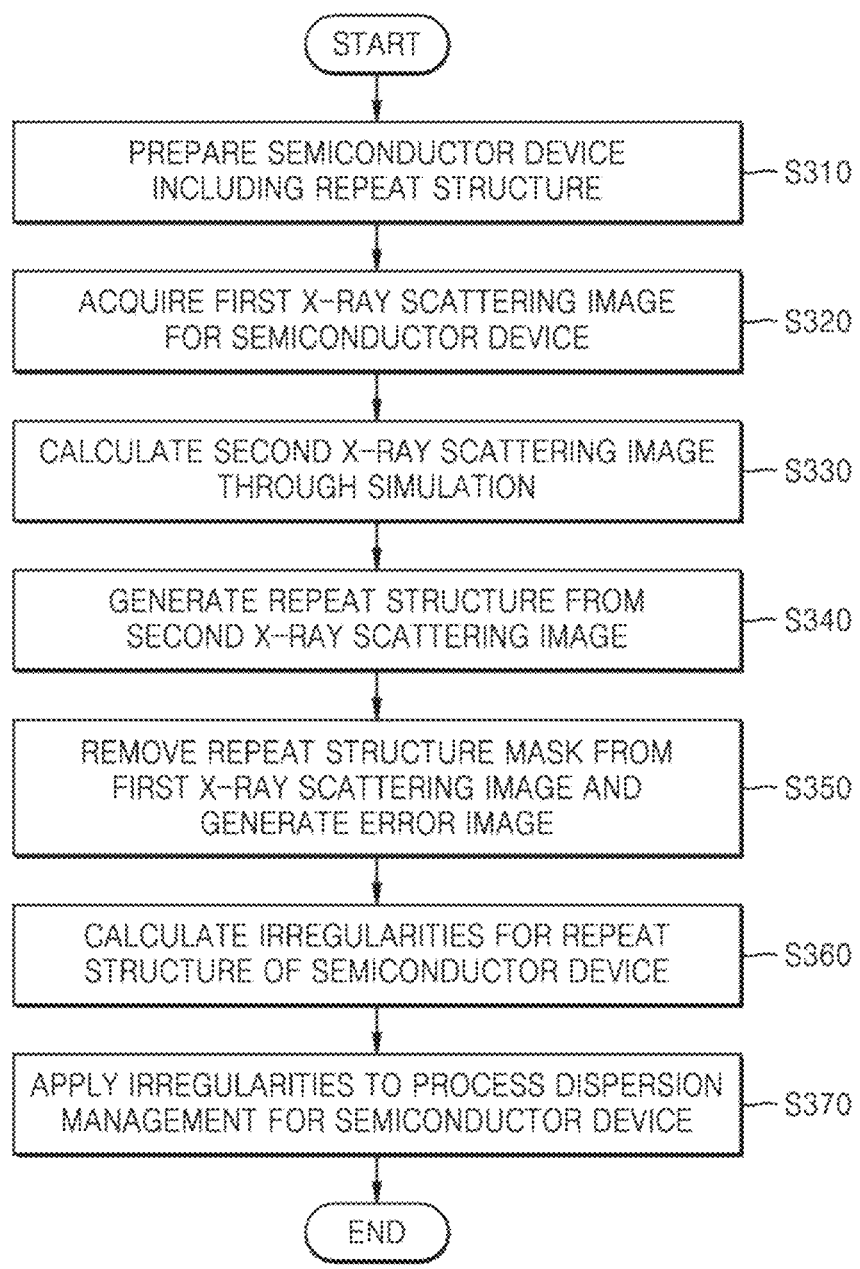
FIG. 8 is a flowchart schematically illustrating a process of a method of manufacturing a semiconductor device including a method of measuring a semiconductor device according to some embodiments.

FIG. 8 is a flowchart schematically illustrating a process of a method of manufacturing a semiconductor device including a method of measuring the semiconductor device according to some embodiments. Portions already described in the description of FIGS. 1 to 7 will be briefly described or omitted for conciseness.

Referring to FIG. 8, the semiconductor device manufacturing method including the semiconductor device measurement method of some embodiments (hereinafter, simply referred to as the semiconductor device manufacturing method) sequentially performs an operation of preparing a semiconductor device including a repeat structure (S310) to an operation of calculating irregularities for the repeat structure (S360). The operation of preparing a semiconductor device including a repeat structure (S310) to the operation of calculating irregularities for the repeat structure (S360) (i.e., the operations S310 to S360) are the same as described with respect to the operation of preparing a semiconductor device including a repeat structure (S110) to an operation of calculating irregularities for the repeat structure (S160) in the semiconductor device measurement method of FIG. 1 (i.e., the operations S110 to S160, respectively).

Thereafter, the irregularities are applied to process dispersion management for the semiconductor device (S370). In the method of manufacturing a semiconductor device according to some embodiments, when the size of an irregularities is out of a predetermined range, the application of the irregularities to the process dispersion management may include a process of analyzing a cause thereof, a process of changing a process condition, based on the analyzed cause, a process of calculating irregularities again with respect to a semiconductor device manufactured according to the changed process condition, and the like.

While various embodiments have been particularly shown and described with reference to the drawings, it will be understood that various changes in form and details may be made therein without departing from the spirit and scope of the following claims.

What is claimed is:

1. A semiconductor device measurement method using X-ray scattering, the semiconductor device measurement method comprising:
   preparing a semiconductor device including a repeat structure;
   irradiating X-rays onto the semiconductor device to obtain a first X-ray scattering image;
   calculating a second X-ray scattering image through simulation, the second X-ray scattering image corresponding to a target repeat structure for the semiconductor device;
   generating a repeat structure mask by analyzing a position of a signal for a regular repeat structure from the second X-ray scattering image;
   removing the repeat structure mask from the first X-ray scattering image and generating an error image; and
   analyzing the error image and calculating irregularities for the repeat structure of the semiconductor device.

2. The semiconductor device measurement method of claim 1, wherein the calculating irregularities comprises calculating a structural dispersion in a field of view (FoV).

3. The semiconductor device measurement method of claim 1, wherein the calculating irregularities comprises quantifying the irregularities with respect to the error image.

4. The semiconductor device measurement method of claim 3, wherein the irregularities are quantified as an average value with respect to a distance based on a center of the error image, or the irregularities are quantified as a value obtained by applying a weight to the distance based on the center of the error image.

5. The semiconductor device measurement method of claim 4, further comprising managing a process dispersion of the semiconductor device based on the quantified irregularities.

6. The semiconductor device measurement method of claim 1, wherein
   the first X-ray scattering image and the second X-ray scattering image are brightest in respective centers thereof due to a diffraction phenomenon, and
   a signal portion due to irregularities is maintained in the error image.

7. The semiconductor device measurement method of claim 1, wherein the repeat structure comprises a high aspect ratio (HAR) structure.

8. The semiconductor device measurement method of claim 1, wherein the repeat structure comprises a storage node of a dynamic random access memory (DRAM), or a channel hole of a vertical NAND (VNAND).

9. The semiconductor device measurement method of claim 1, wherein the first X-ray scattering image and the second X-ray scattering image are obtained by using a small angle X-ray scattering (SAXS) measurement device.

10. The semiconductor device measurement method of claim 1, wherein the preparing comprises preparing a wafer including a plurality of semiconductor devices.

11. A semiconductor device measurement method comprising:
    loading a wafer into a small-angle X-ray scattering (SAXS) measurement device;
    measuring a semiconductor device in the wafer with the SAXS measurement device;
    storing a first X-ray scattering image for the semiconductor device;
    modeling a target repeat structure for the semiconductor device;
    analyzing X-rays with respect to the modeled target repeat structure;
    storing a second X-ray scattering image with respect to the target repeat structure; and
    removing the second X-ray scattering image from the first X-ray scattering image and calculating structural irregularities of a repeat structure of the semiconductor device in an X-ray measurement field of view (FoV),
    wherein the irregularities represent a difference between an actual repeat structure of the semiconductor device and the target repeat structure.

12. The semiconductor device measurement method of claim 11, wherein the storing of the first X-ray scattering image is performed separately from the storing of the second X-ray scattering image, and the calculating the structural irregularities comprises calculating structural dispersion in the FoV.

13. The semiconductor device measurement method of claim 11, wherein the calculating the structural irregularities comprises numerically quantifying the structural irregularities.

14. The semiconductor device measurement method of claim 13, wherein the structural irregularities are quantified as an average value of a distance from a center with respect to an image in the X-ray measurement FoV, or the structural irregularities are quantified as a value obtained by applying a weight to the distance from the center.

15. The semiconductor device measurement method of claim 11, wherein the repeat structure comprises a high aspect ratio (HAR) structure.

16. A semiconductor device manufacturing method comprising:

preparing a semiconductor device including a repeat structure;

irradiating X-rays onto the semiconductor device to obtain a first X-ray scattering image;

calculating a second X-ray scattering image through simulation, the second X-ray scattering image corresponding to a target repeat structure for the semiconductor device;

generating a repeat structure mask from the second X-ray scattering image by analyzing a position of a signal for a regular repeat structure;

removing the repeat structure mask from the first X-ray scattering image and generating an error image;

analyzing the error image and calculating irregularities for the repeat structure of the semiconductor device; and applying the irregularities to a process dispersion management of the semiconductor device.

17. The semiconductor device manufacturing method of claim 16, wherein the calculating irregularities comprises quantifying the irregularities with respect to the error image by calculating structural dispersion in a field of view (FoV).

18. The semiconductor device manufacturing method of claim 17, wherein the irregularities are quantified as an average value with respect to a distance based on a center of the error image, or the irregularities are quantified as a value obtained by applying a weight to the distance based on the center of the error image.

19. The semiconductor device manufacturing method of claim 16, wherein the semiconductor device is a dynamic random access memory (DRAM) or a vertical NAND (VNAND), and the DRAM or the VNAND have a high aspect ratio structure.

20. The semiconductor device manufacturing method of claim 16, wherein:

the first X-ray scattering image and the second X-ray scattering image are brightest in respective centers thereof due to a diffraction phenomenon, and are obtained using a SAXS measurement device, and a signal portion due to irregularities is maintained in the error image.

* * * * *